United States Patent [19]

Dorman et al.

[11] 4,210,723

[45] Jul. 1, 1980

[54] METHOD OF COUPLING A PROTEIN TO AN EPOXYLATED LATEX

[75] Inventors: Linneaus C. Dorman; Inder Mani, both of Midland, Mich.

[73] Assignee: The Dow Chemical Company, Midland, Mich.

[21] Appl. No.: 854,930

[22] Filed: Nov. 25, 1977

Related U.S. Application Data

[63] Continuation-in-part of Ser. No. 708,231, Jul. 23, 1976, abandoned.

[51] Int. Cl.$^2$ .................... C07G 7/00; C07G 7/02; G01N 31/14
[52] U.S. Cl. .................... 435/180; 435/7; 424/12; 23/915; 260/112 R
[58] Field of Search .................... 195/63, 68, DIG. 11, 195/103.5 A, 99; 260/112 R; 424/12; 23/230 B, 915

[56] References Cited

U.S. PATENT DOCUMENTS

| | | | |
|---|---|---|---|
| 3,639,558 | 2/1972 | Csizmas et al | 424/12 |
| 3,806,417 | 4/1974 | Beaucamp et al. | 195/63 |
| 3,821,084 | 6/1974 | Matthews | 195/68 |
| 3,841,970 | 10/1974 | Matthews | 195/63 |
| 3,844,892 | 10/1974 | Matthews | 195/68 |
| 3,849,253 | 11/1974 | Harvey et al. | 195/63 X |
| 3,853,708 | 12/1974 | Porath et al. | 195/68 |
| 3,857,931 | 12/1974 | Hager | 260/112 R X |
| 3,981,775 | 9/1976 | Kenyon et al. | 195/63 X |
| 4,038,140 | 7/1977 | Jaworek et al. | 195/63 |
| 4,048,018 | 9/1977 | Coughlin et al. | 195/63 |
| 4,118,349 | 10/1978 | Bonacker et al. | 195/63 X |

OTHER PUBLICATIONS

Fancoise et al., Copolymerization of Vinyl Aromatic Compounds With $\alpha,\beta$-Unsaturated Epoxy Esters. Chemical Abstracts, vol. 71, 1969, (39646f).
Ludwig et al., Protein-or Peptide-Polystrene Latex Compositions, Chemical Abstracts, vol. 78, 1973 (96019x).

*Primary Examiner*—David M. Naff

[57] ABSTRACT

Proteins are coupled to polymer particles containing free epoxy groups in a latex. The polymer particles are about 0.15 to 1.5 micrometers in diameter, and have an inner core and an outer shell which contains the free epoxy groups. The coupled proteins are particularly useful in carrying out immunological tests.

12 Claims, No Drawings

METHOD OF COUPLING A PROTEIN TO AN EPOXYLATED LATEX

CROSS REFERENCE TO RELATED APPLICATIONS

This application is a continuation-in-part of copending application 708,231 filed July 23, 1976 now abandoned.

FIELD OF THE INVENTION

The invention relates to a method of coupling a latex having surface epoxide groups to a protein or protein component by the formation of an amine bond. Such carrier bound proteins are particularly useful in carrying out immunological tests which are based upon the antigen-antibody reaction.

BACKGROUND OF THE INVENTION

The antigen-antibody reaction is the basis for all immunological test methods. Special proteins called antibodies are produced by an animal in response to the presence of an antigen, that is a foreign substance usually a protein, in the body fluids of the animal. This normal body response to a foreign protein has led to the development of a number of techniques which are used to diagnose various human and animal diseases or disorders. In vitro tests for the presence of a suspected antigen or antibody in a body fluid are carried out by adding the immunological counterpart to a vial of the body fluid, i.e., add antigen if the test is for the presence of antibody or add antibody if the test is for the presence of antigen. If the suspected protein is present, the resulting antigen-antibody reaction is generally manifested by precipitation or agglutination of the antigen-antibody complex.

In some instances the antigen-antibody complex is slow to form and the particles that are formed are too small to be observed with certainty. In such cases, detectability of the antigen-antibody reaction can be improved by utilizing a carrier. When the antigen or antibody is coated onto the surface of a carrier the reaction that occurs with the immunological counterpart produces a visible mass or agglutant. The proteinic antigen or antibody may be adsorbed onto the surface of carriers such as erythrocytes, bacterial cells, bentonite, polystyrene latex particles, anionic phenolic resins, or finely divided diazotized amino cellulose. It has been found, however, that chemical binding of the antigen or antibody molecule to the carrier is superior to physical adsorption. U.S. Pat. No. 3,857,931 teaches that proteinic antigens or antibodies can be chemically bound to a polymer latex carrier having surface carbonyl groups by an amide bond formed in the presence of a water-soluble carbodiimide coupling agent. U.S. Pat. No. 3,806,417 describes a method of bonding a protein to a carrier having an expoxide group. A disadvantage of this method is that the protein must first be reacted with a compound having both an epoxy and olefinic group. The resulting conjugate is the polymerized with another olefinic monomer and bis-olefinic crosslinking agent to form the carrier bound enzyme.

The following references describe methods of bonding a protein to a polymer having an epoxide group: U.S. Pat. Nos. 3,853,708; 3,841,970; 3,844,892 and 3,821,084. The techniques described in these references, however, would not be suitable for use with a latex system.

SUMMARY OF THE INVENTION

The present invention is directed to a process for covalently bonding a protein having a reactive group containing a labile hydrogen atom to a latex having surface epoxide groups. Preferably the reactive group is a free amino group, but other reactive groups such as carboxyl, phenol, hydroxyl, and thiol would also be operable. The coupling occurs when the amino groups of the protein react with the epoxide groups of the latex, usually at a pH of from about 7.0–9.0, to form a new carbon to nitrogen bond, hereafter called an amine bond, binding the protein to the surface of the latex. This process offers a number of advantages over methods of preparing protein-latex conjugates known to the prior art. Specifically, the present method is relatively easy and convenient to carry out. It does not subject the protein to any harsh reaction conditions which may result in distortion or denaturation of the protein molecule. This is especially important since such conformational changes can result in loss of activity. The present method also makes it possible to discharge the residual expoxy groups following binding to the proteins.

As used herein the term latex refers to an aqueous colloidal dispersion of a water insoluble polymer. Latexes used in the practice of the present invention consist of substantially spherical polymer particles having a diameter of between 0.15 and 1.5 micrometers, with from 0.45 to 0.90 micrometers (mM) being preferred. Particle morphology consists of an inner core and a surrounding shell. The core is polymerized or copolymerized from hard monomers as, for example, styrene. The shell is formed by the copolymerization of one or more hard monomers with a copolymerizable ethylenically unsaturated compound having a three-membered exoxy ring. Optionally soft monomer may be copolymerized into the core and/or shell along with the hard monomer to prevent fracturing of the particles.

Preferred emulsion polymerizable monomers for the core are hard monomers which can be polymerized and/or copolymerized with each other in any proportions and/or with other monomers to yield non-film forming polymers. As used herein, non-film forming refers to those polymer particles of the latex which are not film forming or do not coalesce under conditions of use. These monomers include monovinylidene carbocyclic monomers, e.g., styrene, α-methylstyrene, ar-(t-butyl)styrene, ar-methylstyrene, ar,ar-dimethylstyrene, ar-chlorostyrene, ar-(t-amyl)styrene, ar-bromostyrene, ar-fluorostyrene, ar-cyanostyrene, ar-methoxystyrene, ar-ethylstyrene, ar-hydroxymethylstyrene, ar-ethoxystyrene, ar-chloro-ar-methylstyrene, ar,ar-dichlorostyrene, ar,ar-difluorostyrene, vinyl naphthalene, and other such emulsion polymerizable monomers having not more than 26 carbon atoms; esters of α,β-ethylenically unsaturated carboxylic acids which polymerize to form non-film forming polymers, e.g., methyl methacrylate, chloroethyl methacrylate, n-butyl methacrylate, ethyl methacrylate, isobutyl methacrylate, isopropyl methacrylate, phenyl methacrylate, butyl chloroacrylate, cyclohexyl chloroacrylate, ethyl chloroacrylate, methyl chloroacrylate, isopropyl chloroacrylate and other such esters capable of being polymerized to form hard polymers; α,β-ethylenically unsaturated esters of non-polymerizable carboxylic acids, e.g., vinyl benzoate, vinyl toluate, vinyl ar-ethylbenzoate, allyl ar-ethylbenzoate, vinyl trimethylacetate, vinyl pivalate, vinyl trichloroacetate and other such monomers wherein the unsaturated moiety has from 2 to 14 carbon atoms and the acid moiety has from 2 to 12 carbon atoms; $\alpha,\beta$-ethylenically unsaturated nitriles, e.g., such as nitriles having not more than 12 carbon atoms; other polymerizable vinyl monomers such as vinyl chloride, vinyl bromide and the like. Of the foregoing monomers, the monovinylidene carbocyclic aromatic monomers, particularly styrene and mixtures of styrene, methyl methacrylate and acrylonitrile, are especially preferred.

Soft monomers which may be optionally added include the alkyl acrylates such as ethylacrylate, butylacrylate, or 2-ethylhexyl acrylate; the higher alkyl methacrylates such as hexyl methacrylate or 2-ethylhexyl methocrylate; and the conjugated dienes such as isoprene or butadiene.

Preferred monomer for the copolymer of the shell is a mixture of one or more hard monomers as described above and a copolymerizable ethylenically unsaturated compound having a three-membered epoxy ring.

Representative epoxy monomers include unsaturated alkyl glycidyl esters, unsaturated alkyl glycidyl ethers, unsaturated cycloalkyl glycidyl ethers, unsaturated alkyl-substituted phenyl glycidyl ethers, and the monoepoxide compounds of the diene type monomers.

Suitable glycidyl esters include glycidyl methacrylate, glycidyl acrylate, glycidyl esters of crotonic acid and long chain unsaturated fatty acids and the like; unsaturated alkyl glycidyl ethers include vinyl glycidyl ether, isopropenyl glycidyl ether, oleyl glycidyl ether, allyl and methallyl glycidyl ethers and the like; unsaturated cycloalkyl and phenyl glycidyl ethers include 4-vinyl cyclohexyl glycidyl ether, p-vinylbenzyl glycidyl ether, o-allyl phenylglycidyl ether, and the like; the monoepoxide compounds of the diene type monomers include butadiene monoepoxide, chloroprene monoepoxide, 3,4-epoxy-1-pentene, 4,5-epoxy-1-pentene, 4,5-epoxy-2-pentene, 4,5-epoxy-1-hexene, 3,4-epoxy-1-vinylcyclohexene and divinylbenzene monoxide, and the like.

The exact amount of the epoxy monomer needed to prepare latexes of this invention is dictated by the population of surface epoxy groups needed for optimal coupling with the desired protein. For example, for coupling human chorionic gonadotropin to a styrene-glycidyl methacrylate latex a coupling site density of about one epoxy unit per 5 to 40 square angstrom units ($A^{\circ 2}$) gives satisfactory results with about one epoxy unit per 8 to 20 $A^{\circ 2}$ being preferred. This same coupling site density would also be operable for other proteins such as, for example, insulin.

In preparing latex bound proteins for use in immunological testing it has been found that monodispersed latexes, that is latexes having substantially uniform particle sizes, are preferred because uniformity of size assures an equal statistical distribution of antigen or antibody molecules on the surface of the latex particles. For a given weight of polymer, the total surface area of latex will increase with a decrease in the size of the particles and vice versa. Thus, in a latex containing a distribution of various particle sizes the smaller particles will have a greater surface area and, consequently, more total reaction sites than the larger particles. The unequal distribution of antigen or antibody on the latex particles will lead to unequal agglutination of particles and poorly defined diagnostic results.

Another advantage of using uniform latex particles as diagnostic agents is that they are better suited for instrumental analysis. Particles of the same size will flocculate, agglutinate, or settle at the same rate whereas different sized particles will agglutinate at variable rates. Thus an instrumental method based on the absorption or transmission of light through an agglutinating latex suspension will be more accurate, more reproducible, and easier to standardize and read with uniform latex particles than with latexes having varied particle sizes. Conjugates of human chorionic gonadotropin bound to styrene glycidyl methacrylate latex using the present invention have showed substantially no change in immunological activity after storage for as long as twelve months at about 4°–6° C.

DETAILED DESCRIPTION OF THE INVENTION

The following examples describe the preparation of three monodispersed styrene-glycidyl methacrylate latexes. Commercially available monodispersed polystyrene latexes were capped with a mixture of styrene and glycidyl methacrylate. Unless otherwise indicated amounts are expressed as parts by weight.

EXAMPLE 1

The following ingredients were added into a one liter three-necked flask equipped with a stirrer, a nitrogen inlet tube and a condenser.

|  | Dry Weight Parts | Wet Weight Parts |
|---|---|---|
| Polystyrene latex |  |  |
| (particle size 0.76 micrometer) | 60.5 | 188 |
| Dihexyl sodium sulfosuccinate | 0.3 | 6 |
| Potassium persulfate | 0.3 | 6 |
| Sodium bicarbonate | 0.3 | 6 |
| Styrene | 45 | 45 |
| Glycidyl methacrylate | 15 | 15 |
| Water | — | 134 |

The reaction mixture was stirred and the flask was purged with nitrogen for about 10 to 20 minutes. The temperature of the reaction was brought to 65° C. and held at that temperature for four hours while maintaining a positive nitrogen pressure. The resulting latex was cooled and filtered. The average particle size of the latex was determined by electron microscopy and found to be about 0.91 $\mu M$ in diameter.

EXAMPLE 2

Using the general procedure outlined in Example 1 above the following ingredients were used to prepare a monodispersed latex having an average particle size of about 0.59 $\mu M$ in diameter.

|  | Dry Weight Parts | Wet Weight Parts |
|---|---|---|
| Polystyrene latex |  |  |
| (particle size 0.508 micrometer) | 30.1 | 95 |
| Dihexyl sodium sulfosuccinate | 0.15 | 3 |
| Potassium persulfate | 0.15 | 3 |
| Sodium bicarbonate | 0.15 | 3 |
| Styrene | 15 | 15 |
| Glycidyl methacrylate | 15 | 15 |
| Water | — | 266 |

EXAMPLE 3

The following ingredients were used to prepare a monodispersed latex having an average particle size of 0.20 μM in diameter. The same general procedure was used as described above.

|  | Dry Weight Parts | Wet Weight Parts |
| --- | --- | --- |
| Polystyrene latex (particle size 0.176 micrometer) | 30 | 300 |
| Dihexyl sodium sulfosuccinate | 0.15 | 3 |
| Potassium persulfate | 0.15 | 3 |
| Sodium bicarbonate | 0.15 | 3 |
| Styrene | 15 | 15 |
| Glycidyl methacrylate | 15 | 15 |
| Water | — | 61 |

The epoxy content of the latex expressed as milliequivalents oxirane groups per gram

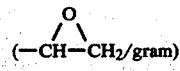

and as square angstrom units per one oxirane group was determined for each latex prepared above. The results are shown in Table I below.

TABLE I

| Latex Ex. No. | Particle Size (μM) | A·²/—CH—CH₂ (epoxide) | —CH—CH₂/gram mequiv (epoxide) |
| --- | --- | --- | --- |
| 1 | .907 | 15.0 | 0.07 |
| 2 | .592 | 9.4 | 0.17 |
| 3 | .201 | 17.0 | 0.278 |

Milliequivalents of oxirane groups per gram of polymer were determined by treating the latex containing a known amount of polymer with known equivalents of hydrogen iodide. The residual hydrogen iodide remaining in the latex was titrated with standarized silver nitrate solution to determine the amount of hydrogen iodide that reacted with the epoxy groups. Millequivalents of epoxy groups were then determined from this information.

The latexes prepared above were found to be suitable for use in the practice of the present invention. Samples from each of the latex preparations described above were coupled with human chorionic gonadotropin, hereafter called HCG. This hormone is a glycoprotein and governs the production and secretion of progesterone by the corpus luteum. It is normally secreted by the chorionic tissue of the placenta during pregnancy. Latex-bound HCG is useful in the detection of pregnancy.

EXAMPLE 4

A solution containing 5000IU of HCG in 7 ml of pH 8.0 phosphate buffer (I=0.05; 0.1 M NaCl 1:10,000 thimerosal) was added with stirring to a siliconized 25 ml round bottomed flask already containing 1.61 grams of styrene-glycidyl methacrylate prepared as described in Example 1 above. The resulting latex suspension was stirred 4 days in a cold room (5° C.). The reaction mixture was washed by membrane filtration for about 3 hours in a Diaflo ® filter cell with 145 ml of phosphate buffer. The washed latex and rinse was dialyzed in cellophane against pH 8.2, 0.1 M glycine buffer. After two days of dialysis 16.4 grams of the styrene-glycidyl methacrylate latex-HCG product was obtained having a detection sensitivity of 0.9 IU/HCG/ml..

EXAMPLE 5

This product was prepared in an identical manner as Example 4 except for the following exceptions. The reaction mixture was treated after 3 days with 1 ml of pH 8.2 glycine buffer to discharge the residual epoxy groups. After stirring for 1 more day in the cold, 9.9 grams of the reaction mixture was washed by membrane filtration using 188 ml of pH 7.0 phosphate buffer (I=0.05; 0.1 M NaCl). The resulting product and rinse were treated with 13 mg of sodium azide as a preservative. The resulting product had a detection sensitivity of 1.8 IU/HCG/ml..

EXAMPLE 6

Latex prepared according the procedure of Example 2 above (3.08 grams of latex, 0.46 gram polymer) was placed in a 25 ml round bottomed flask equipped with a Teflon ® coated magnetic stirring bar. A solution containing 5000 IU of HCG in 8 ml of cold, pH 8 phosphate buffer (I=0.05; 0.0 M NaCl; 0.01 percent thimerosal) was added slowly to the flask. The reaction was stirred gently for 90-96 hours at about 5° C. The latex-HCG conjugate was washed with 110-115 ml of phosphate buffer by ultrafiltration for about 70-110 minutes. The combined latex-HCG and rinses were dialyzed in cellophane at 5° C. for 24 hours. Product prepared by this procedure showed a detection sensitivity of 0.9-1.8 IU HCG/ml..

Using the procedures already described HCG was coupled to latex prepared in Example 3 above. Using the general procedures and methods already described additional samples of HCG-latex conjugate were prepared. The factors which were found to significantly affect the quality of the final product are summarized below.

The examples above illustrate the operation of the present invention. Other factors which have been observed to effect the coupling of HCG to the styrene-glycidyl methacrylate monodispersed latexes described above were the age of the latex and the means of storage of the latex prior to coupling. The latex should be stored under refrigeration and used in coupling reactions as soon as convenient. The latex prepared in Example 2 above was found to behave satisfactorily in the coupling reaction with HCG after storage for as long as one month under refrigeration.

In preparing immunologically active latex-HCG conjugates it was found that the source of HCG was an important variable in determining sensitivity. HCG preparations from various commercial sources should be checked to see which is most satisfactory for the particular applications. Although varying amounts of protein may be coupled to the latex, attaching maximum amounts of HCG to the latex did not produce optimal results. Although other amounts were operable, the preferred amount of HCG used in the coupling reaction was about 1,000-25,000 I.U. per gram of polymer with about 11,000 I.U./gram polymer particularly preferred. The preferred reaction concentration of polymer solids was about 4-5%.

In general, the coupling reaction is carried out at a pH of from about 7.5-8.5 with a pH of about 8.0 preferred. A phosphate buffer is generally used to couple HCG to the latex. Borate buffers are generally unsatisfactory with proteins such as HCG which have a high carbohydrate content. It was also discovered that the coupling reaction time could be reduced to about one day or less by conducting the reaction at room temperature instead of 5° C. as shown in the examples above. However, where no special refrigerated facility is used, appropriate control of potential microbial contaminants is required.

Following coupling of the latex to the HCG, it is essential that unreacted HCG and other impurities be removed from the reaction mixture. Ultrafiltration followed by cellophane dialysis or high-speed centrifugation followed by cellophane dialysis gave a satisfactory product. Hollow-fiber dialysis although still operable was less effective in removing the excess HCG from the reaction mixture.

If the final latex-HCG conjugate is buffered with the preferred 8.2 glycine buffer, it is unnecessary to discharge the residual epoxy groups. If, however, a neutral buffer system is desired, an extra step to discharge the residual epoxy groups is desirable (as illustrated in Example 5 above).

In general, it was found that aging the final latex-HCG conjugate significantly improved the immunological activity of the product. The aging period required to obtain optimal immunological activity depends on the temperature at which the aging occurs, i.e. the lower the temperature the longer the aging period. It was found that product aged for 3 to 5 days at about 25° C. gave satisfactory performance. Product stored at about 5° C. required storage for about two weeks to achieve optimal activity.

The latex-HCG conjugate may be combined into a kit containing all the necessary reagents for immunologically testing for pregnancy. Such a kit would contain a first reagent composition comprising the latex-HCG conjugate described above and a second reagent composition comprising buffered anti-HCG serum, generally obtained from New Zealand white rabbits. See $J.$ $Clin.$ $Endocr.$ 33, 988 (1971). The basic reagents may also be combined with ancillary components such as an opaque glass slide with recessed mixing areas and an applicator stick.

It may also be desirable when the conjugate is intended for immunological purposes to dye the latex particles prior to coupling with the protein to aid in the detection of agglutination. This is readily accomplished by mixing the latex with a dye solution containing a solvent which is able to penetrate the latex particles. For example, Calco Oil Blue N dye (American Cyanamid) dissolved in benzene was found to give satisfactory results. The benzene was removed in an evaporator prior to coupling with the protein.

The following example illustrates the coupling of styrene-glycidyl methacrylate latex to insulin.

EXAMPLE 8

Latex prepared as described in Example 1 above (2.5 grams of latex, 0.75 grams of polymer) was placed in a flask to which 2.5 ml of insulin solution (15 mg of insulin) and 5 drops of 0.1 N sodium hydroxide were added. The final pH was 8. The reaction mass was stirred at 5° C. for 90 hours whereupon 4.4 grams of the latex reaction mixture (4.8 grams) was washed by membrane filtration in a Diaflo ® filter cell using 0.1μ Millipore filter and pH 8 borate buffer. A hydrodynamic pressure up to about 50 p.s.i.g. was used and the effluent was scanned by U.V. for the presence of uncoupled insulin. The filtration was continued until no insulin was detected in the effluent. Thin layer electrophoresis confirmed the insulin was chemically bound to the latex.

EXAMPLE 9

Latex prepared as described in Example 1 above (6.3 grams of latex, 0.92 grams of polymer) was added to a solution containing 7.33 mg of horseradish peroxidase in 10 ml of pH 8 phosphate saline buffer. The mixture was covered and stirred for about 5 days at 5° C. The reaction mixture was diluted (2–3x) with buffer and centrifuged at 18,000 rpm for about 35 minutes. The supernatant was discarded and the latex-peroxidase residue was resuspended in pH 7 phosphate saline buffer with 1% surfactant added. The centrifugation and resuspension was repeated two more times using pH 7 phosphate saline buffer without surfactant. The latex peroxides conjugate was filtered through a thin mat of glass wool to obtain the final product. The resulting conjugate was tested for enzymatic peroxidase activity using a modification of the method of Steinman et al. [$J.$ $Cell.$ $Biol.$ 55, 186 (1972)]. Three samples of product plus one sample of product supernatant were allowed to react for different time intervals with substrate containing dianisidine dihydrochloride and hydrogen peroxide in a pH 7 phosphate saline buffer. Reaction mixtures were filtered and the filtrates were scanned at 400 nanometers. The results were as follows:

| Sample | Reaction Time (min:sec) | Optical Density* |
|---|---|---|
| 1 | 4:55 | 0.53 |
| 2 | 5:17 | 0.62 |
| 3 | 9:17 | 0.65 |
| 4 (supernatant) | 10:13 | 0.005 |

*scanned at 400 nanometers

The data show very little enzymatic activity (oxidation of dianisidine) in the supernatant reaction mixture (sample #4). Thus, enzymatic activity of the latex-peroxidase product was due essentially to enzyme immobilized on the latex particles and not to soluble residual peroxidase in the supernatant.

We claim:

1. A method for coupling a protein having a reactive group containing a labile hydrogen to polymer particles containing free epoxy groups in a latex wherein the polymer particles in the latex range in size from about 0.15 to 1.5 micrometers in diameter and have an inner core and an outer shell containing free epoxy groups, said inner core being formed by the polymerization or copolymerization of one or more hard monomers and optionally soft monomer to produce a latex containing polymer particles that are said inner core and said outer shell being formed by copolymerization in the presence of said inner core polymer particles one or more hard monomers and a copolymerizable ethylenically unsaturated compound having free epoxy groups and optionally soft monomer, said method comprising reacting said polymer particles containing free epoxy groups in the latex and said protein at a pH of 7.0–9.0 for a time sufficient to form a covalent bond between the reactive group of the protein and the free epoxy group of the polymer particles and removing the unreacted protein from the latex-protein conjugate.

2. The method of claim 1 wherein the latex containing the polymer particles having free epoxy groups is a monodispersed latex and the reactive group on the protein is amino.

3. The method of claim 1 wherein the outer shell on the polymer particles present in the latex is styrene-glycidyl methacrylate copolymer.

4. The method of claim 3 wherein the protein is human chorionic ganadotropin.

5. The method of claim 3 wherein the protein is insulin.

6. The method of claim 3 wherein the protein is an enzyme.

7. The method of claim 4 wherein the coupling site density of the styrene-glycidyl methacrylate copolymer outer shell is about one epoxy unit per 5 to 40 square angstrom units of particle surface area and the amount of human chorionic gonadotropin used to prepare the polymer particle protein conjugate is 1,000 to 25,000 international units per gram of polymer particles.

8. A protein polymer particle conjugate in a latex formed by the method of claim 2.

9. The protein-latex conjugate of claim 8 wherein the protein is human chorionic gonadotropin.

10. The protein-polymer particle conjugate in a latex of claim 8 wherein the protein is insulin and the latex contains polymer particles having an outer shell of styrene-glycidyl methacrylate copolymer.

11. The protein polymer particle conjugate in a latex of claim 8 wherein the latex is dyed.

12. A kit for immunologically testing for pregnancy which comprises as a first reagent the protein-polymer particle conjugate in a latex of claim 9 and as a second reagent, anti-human chorionic gonadotropin serum.

* * * * *